United States Patent
Chen et al.

(10) Patent No.: US 9,755,154 B2
(45) Date of Patent: *Sep. 5, 2017

(54) SPIRALLY CONFIGURED CIS-STILBENE/FLUORENE HYBRID MATERIALS FOR ORGANIC LIGHT-EMITTING DIODE

(71) Applicant: NICHEM FINE TECHNOLOGY CO., LTD., Jhubei, Hsinchu County (TW)

(72) Inventors: Chien-Tien Chen, Hsinchu (TW); Jwo-Huei Jou, Hsinchu (TW)

(73) Assignee: Nichem Fine Technology Co., Ltd., Zhubei/Hsinchu County (TW)

(*) Notice: Subject to any disclaimer, the term of this patent is extended or adjusted under 35 U.S.C. 154(b) by 0 days.

This patent is subject to a terminal disclaimer.

(21) Appl. No.: 14/583,617

(22) Filed: Dec. 27, 2014

(65) Prior Publication Data
US 2016/0111648 A1    Apr. 21, 2016

(30) Foreign Application Priority Data

Oct. 15, 2014 (TW) ................ 103135652 A

(51) Int. Cl.
| | |
|---|---|
| *H01L 51/00* | (2006.01) |
| *C07C 255/52* | (2006.01) |
| *C07C 255/51* | (2006.01) |
| *C07C 255/58* | (2006.01) |
| *H01L 51/50* | (2006.01) |

(52) U.S. Cl.
CPC ........ *H01L 51/0056* (2013.01); *C07C 255/52* (2013.01); *C07C 255/58* (2013.01); *H01L 51/0058* (2013.01); *H01L 51/5072* (2013.01); *C07C 2103/30* (2013.01); *H01L 51/5096* (2013.01); *H01L 2251/308* (2013.01); *Y02E 10/549* (2013.01)

(58) Field of Classification Search
CPC . C06B 47/10; C07F 5/027; C07F 5/02; A01N 37/34; A01N 53/00; H01L 51/0056; H01L 51/0058; C07C 255/52; C07C 255/51

USPC ......................................................... 558/384
See application file for complete search history.

(56) References Cited

U.S. PATENT DOCUMENTS 8,921,844 B2 * 12/2014 Chen .................... H01L 51/006
                                                              257/40

FOREIGN PATENT DOCUMENTS

JP       2010024149 A   *  2/2010

OTHER PUBLICATIONS

Chen, C., W. Chao, H. Liu, Y. Wei, J. Jou, and S. Kumar "Spirally configured cis-stilbene/fluorene hybrids as ambipolar, fluorescent materials for organic light emitting diode applications" RSC Adv. 2013, 3: pp. 9381-9390.*
Chen, Chien-Tien, Prof. "Spirally Configured Cis-Stilbene/Fluorene (STIF) Hybrids as Electron-transporting Type Emitters for OLED Applications and as Dyes or Hole-Transporting Materials for Solar Cell Applications." Irregular Physics Seminars. Hsinchu, Taiwan, Jun. 1, 2013. Lecture. (1 page).

* cited by examiner

*Primary Examiner* — Matthew Coughlin
*Assistant Examiner* — Sagar Patel
(74) *Attorney, Agent, or Firm* — Muncy, Geissler, Olds & Lowe, P.C.

(57) ABSTRACT

The present invention provides a series of spirally configured cis-stilbene/fluorene hybrid materials, which are spirally-configured cis-stilbene/fluorene derivatives having glass transition temperatures ranged from 105° C. to 130° C., decomposition temperatures ranged from 385° C. to 415° C., reversible electron transport property, and balanced charges motilities. Moreover, a variety of experimental data have proved that the yellow fluorescent, the green phosphorescent, the yellow phosphorescent, and the red phosphorescent OLEDs using this spirally configured cis-stilbene/fluorene derivatives as the electron transport layers having hole blocking functions can indeed show excellent EQE, current efficiency, power efficiency, maximum luminance, and device lifetime performances much better than the conventional or commercial yellow fluorescent, green phosphorescent, yellow phosphorescent, and red phosphorescent OLEDs.

9 Claims, 1 Drawing Sheet

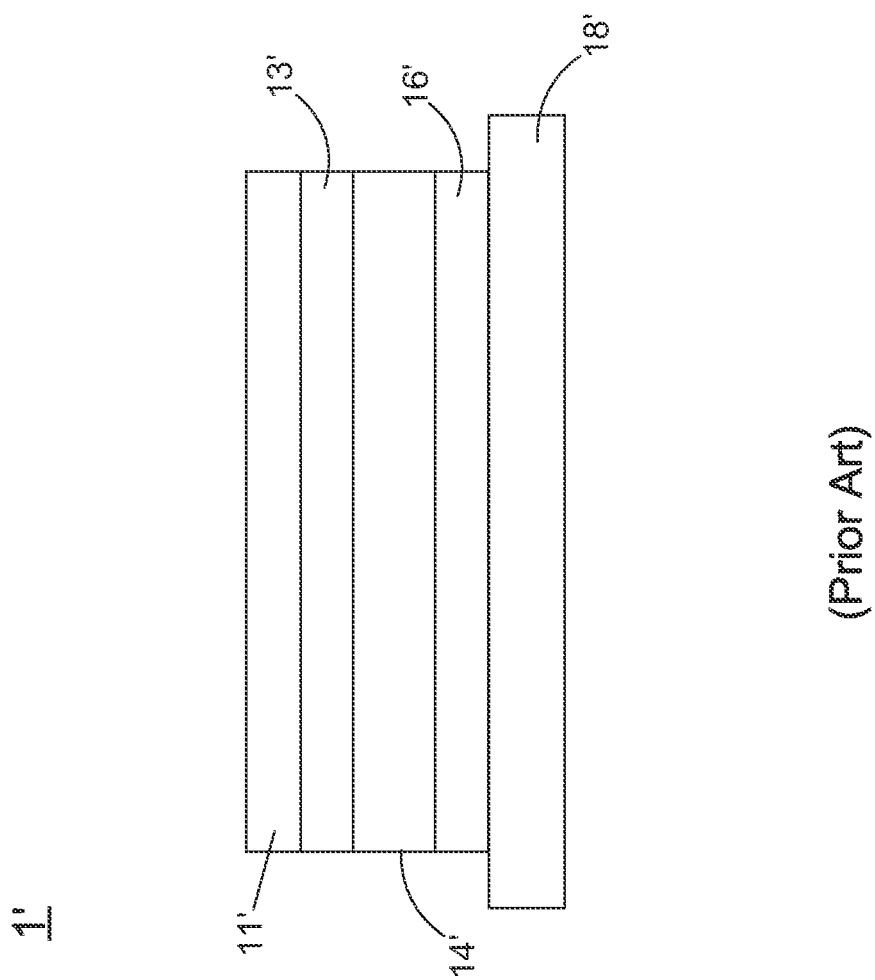

SPIRALLY CONFIGURED CIS-STILBENE/FLUORENE HYBRID MATERIALS FOR ORGANIC LIGHT-EMITTING DIODE

BACKGROUND OF THE INVENTION

1. Field of the Invention

The present invention relates to the technology field of carrier transport materials, and more particularly to a spirally configured cis-stilbene/fluorene hybrid material for OLEDs.

2. Description of the Prior Art

It is well known that organic light emitting diode (OLED) was initially invented and proposed by Eastman Kodak Company through a vacuum evaporation method. Tang and VanSlyke of Kodak Company deposited an electron transport material such as $Alq_3$ on a transparent indium tin oxide (abbreviated as ITO) glass formed with an organic layer of aromatic diamine thereon, and subsequently completed the fabrication of an organic electroluminescent (EL) device after a metal electrode is vapor-deposited onto the $Alq_3$ layer. The organic EL device currently becomes a new generation lighting device or display because of high brightness, fast response speed, light weight, compactness, true color, no difference in viewing angles, without using any LCD backlight plates, and low power consumption.

Recently, some interlayers such as electron transport layer and hole transport layer are added between the cathode and the anode for increasing the current efficiency and power efficiency of the OLEDs. For example, an organic light emitting diode (OLED) 1' shown as FIG. 1 is designed to consist of: a cathode 11', an electron injection layer 13', a light emitting layer 14', a hole transport layer 16', and an anode 18'.

In device function concept, the light emitted by the OLED 1' is resulted from excitons produced by the recombination of electrons and holes in the light emitting layer 14'. However, according to theoretical speculation, the ratio of the excitons with singlet excited state and the excitons with triplet excited state is 3:1. So that, when a small molecular fluorescent material is used as the light-emitting layer 14' of the OLED 1', there are about 25% excitons being used in emitting light, and the rest of 75% excitons with triplet excited state are lost through non-luminescence mechanism. For this reason, the general fluorescent material performs a maximum quantum yield of 25% in limit which amounts to an external quantum efficiency of 5% in the device.

Moreover, researches further find that certain hole transport material can simultaneously perform electron confining ability, such as the material represented by following chemical formulas 1' and 2'. The chemical formula 1' represents the chemical structure of Tris(4-carbazoyl-9-ylphenyl)amine, which is called TCTA in abbreviation. The chemical formula 2' represents the chemical structure of N,N'-Di(1-naphthyl)-N,N'-diphenyl-(1,1'-biphenyl)-4,4'-diamine called NPB in abbreviation.

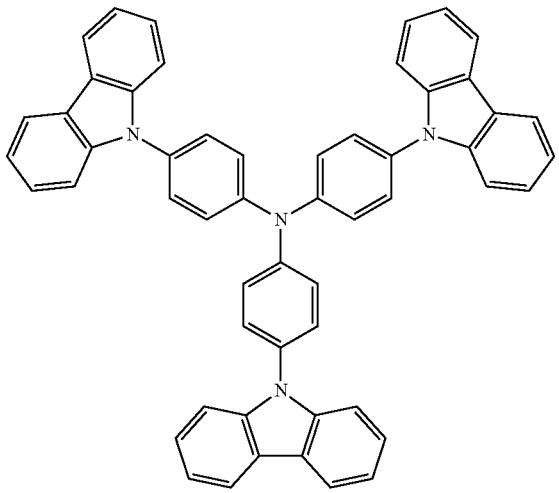

[chemical formula 1']

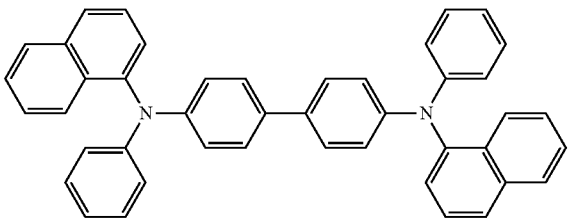

[chemical formula 2']

Recently, for effectively increasing the lighting performance of OLEDs, OLED manufactures and researchers have made great efforts to develop electron transport materials with hole blocking functionality, such as TmPyPb, TPBi, 3TPYMB, BmPyPb, and DPyPA. Wherein TmPyPb is the abbreviation of 3,3'-[5'-[3-(3-Pyridinyl)phenyl][1,1':3',1"-terphenyl]-3,3"-diyl]bispyridine, TPBi is the abbreviation of 1,3,5-Tris(1-phenyl-1H-benzimidazol-2-yl)benzene, 3TPYMB is the abbreviation of Tris(2,4,6-triMethyl-3-(pyridin-3-yl)phenyl)borane, BmPyPb is the abbreviation of 1,3-bis(3,5-dipyrid-3-yl-phenyl)benzene, and DPyPA is the abbreviation of 9,10-bis(3-(pyridin-3-yl)phenyl)anthracene.

In spite of various electron transport materials with hole blocking functionality have been developed, the phosphorescence OLEDs applied with the said electron transport materials still cannot perform outstanding luminous efficiency and device lifetime. Accordingly, in view of the conventional or commercial electron transport materials with hole blocking functionality still including drawbacks, the inventor of the present application has made great efforts to make inventive research thereon and eventually provided a spirally configured cis-stilbene/fluorene hybrid materials for organic light-emitting diode.

SUMMARY OF THE INVENTION

The primary objective of the present invention is to provide a spirally configured cis-stilbene/fluorene hybrid material, which is a spirally-configured cis-stilbene/fluorene derivative having a glass transition temperature ranged from 105° C. to 130° C., a decomposition temperature ranged from 385° C. to 415° C., reversible electron transport property, and balanced charges motilities. Moreover, a variety of experimental data have proved that the yellow fluorescent, the green phosphorescent, the yellow phosphorescent, and the red phosphorescent OLEDs using this spirally configured cis-stilbene/fluorene derivative as the electron transport layer having hole blocking functionality can indeed perform excellent EQE, current efficiency, power efficiency, maximum luminance, and device lifetime better than yellow fluorescent, green phosphorescent, yellow phosphorescent, and red phosphorescent OLEDs based on the conventional or commercial electron transport materials.

Accordingly, in order to achieve the primary objective of the present invention, the inventor of the present invention provides a spirally configured cis-stilbene/fluorene hybrid material for OLEDs, wherein the spirally configured cis-stilbene/fluorene hybrid material is a spirally-configured cis-stilbene/fluorene derivative having the functionality to block holes and constructed by at least one cis-Stilbene based component and at least one fluorene based component.

According to one embodiment of the spirally configured cis-stilbene/fluorene hybrid material, wherein the said spirally-configured cis-stilbene/fluorene derivative is represented by following chemical formula I:

[chemical formula I]

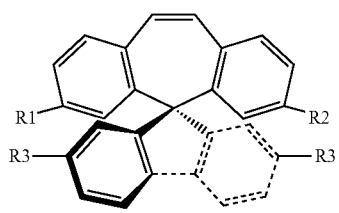

wherein R1 is diphenylamino (—NPh$_2$), and R2 is selected from the group consisting of following chemical formula I-1, chemical formula I-2-1, chemical formula I-2-2, and chemical formula I-2-3:

[chemical formula I-1]

—CN

[chemical formula I-2-1]

[chemical formula I-2-2]

[chemical formula I-2-3]

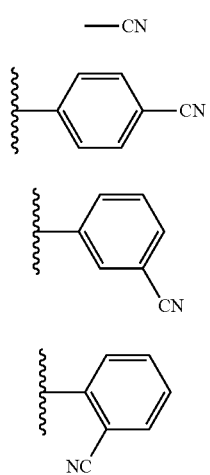

wherein R3 is selected from the group consisting of following chemical formula I-3 and chemical formula I-4:

[chemical formula I-3]

—H

[chemical formula I-4]

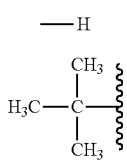

wherein the chemical formula I-3 and the chemical formula I-4 are respectively the chemical structure of hydrogen group and tert-butyl group.

According to one embodiment of the spirally configured cis-stilbene/fluorene hybrid material, wherein the spirally configured cis-stilbene/fluorene hybrid material is represented by following chemical formula II, chemical formula III, chemical formula IV, and chemical formula V:

[chemical formula II]

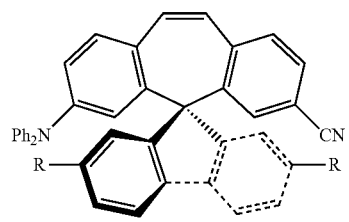

[chemical formula III]

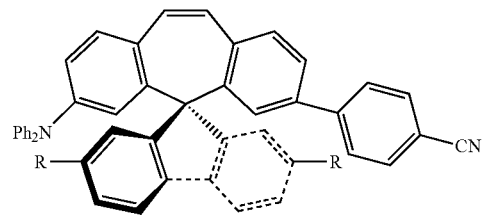

[chemical formula IV]

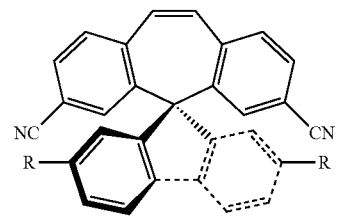

[chemical formula V]

wherein R is hydrogen group or tert-butyl group.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein:

FIG. 1 is a framework view of a conventional organic light emitting diode (OLED).

DETAILED DESCRIPTION OF THE PREFERRED EMBODIMENTS

To more clearly describe spirally configured cis-stilbene/fluorene hybrid materials for OLEDs according to the present invention, embodiments of the present invention will be described in detail with reference to the attached drawings hereinafter.

The present invention provides a spirally configured cis-stilbene/fluorene hybrid material for OLEDs. The spirally configured cis-stilbene/fluorene hybrid material, constructed by at least one cis-Stilbene based component and at least one fluorene based component, is a spirally-configured cis-stilbene/fluorene derivative having the functionality to block holes. This spirally configured cis-stilbene/fluorene hybrid material is mainly applied in an OLED for being as an electron transport layer and/or a hole blocking layer; moreover, this spirally configured cis-stilbene/fluorene hybrid material can also be applied in a solar cell for being as a carrier transport layer.

In the present invention, the said spirally-configured cis-stilbene/fluorene derivative is represented by following chemical formula I:

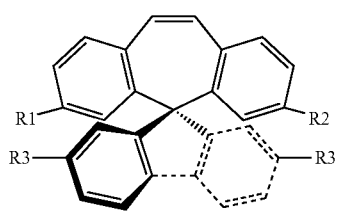

[chemical formula I]

In the chemical formula I, R1 is diphenylamino (—NPh$_2$), and R2 is the following chemical formula I-1, chemical formula I-2-1, chemical formula I-2-2, or chemical formula I-3. Moreover, R3 is the following chemical formula I-4 (i.e., hydrogen group) or chemical formula I-4 (i.e., tert-butyl group).

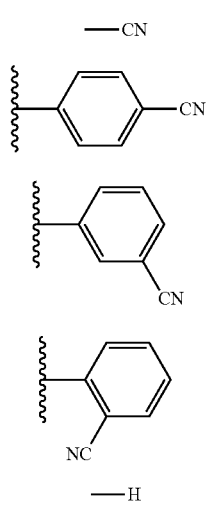

[chemical formula I-1]
[chemical formula I-2-1]
[chemical formula I-2-2]
[chemical formula I-2-3]]
[chemical formula I-3]

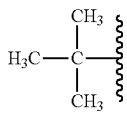

[chemical formula I-4]

To manufacture the spirally configured cis-stilbene/fluorene hybrid material of the present invention, a key intermediate product needs to be firstly fabricated by using following steps:

(1) dissolving 30 mM 2-Bromobiphenyl of 5.2 mL in 100 mL of anhydrous tetrahydrofuran (THF);

(2) placing the solution obtained from the step (1) in an environment of 78° C. for standing;

(3) taking 12 mL of butyllithium hexanes solution (30 mM) from a n-butyllithium solution 2.5 M in hexanes, and then adding the 12 mL butyllithium hexanes solution dropwise into the solution obtained from the step (2) and stirring for 30 min;

(4) dissolving 20 mM 3,7-dibromo-dibenzosuberenone of 7.28 g in 60 mL of anhydrous THF;

(5) adding the solution obtained from step-4 to the reaction mixture in step-3 dropwise;

(6) adding 10 mL of saturated aqueous sodium bicarbonate solution into the product obtained from the step (5) for executing a quenching reaction, and then remove the THF by rotary evaporation;

(7) treating the product obtained from the step (6) with a extracting process by using dichloromethane, and then obtaining a liquid extract;

(8) adding 5 g magnesium sulfate into the liquid extract, and then treat a drying process and a filtering process to the liquid extract sequentially; and (9) using a rotary evaporating process to the product obtained from the step (8), so as to obtain an intermediate product.

Furthermore, the following steps can be used for making another intermediate product to clear crystalline material.

(10) dissolving the intermediate product from step (9) in 60 m acetic acid;

(11) adding 1 mL of concentrated hydrochloric acid (12 N) into the solution obtained from the step (10);

(12) letting the solution mixture obtained from the step (11) to react for 2 hours at 120° C. by using a reflux device;

(13) cooling the temperature of the product obtained from the step (12) down to 0° C.;

(14) adding 60 mL hexane into the product obtained from the step (13);

(15) using a Buchner funnel to treat the product obtained from the step (14) with a filtering process, so as to obtain a precipitate;

(16) using hexane to wash the precipitate for 3 times, so as to obtain a solid material;

(17) using dichloromethane/hexane to treat the solid with a recrystallization process for obtaining clear crystal solid, wherein the clear crystal solid is presented by following chemical formula 1.

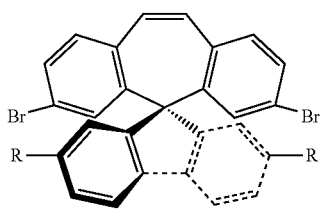

[chemical formula 1]

Furthermore, various exemplary embodiments for the spirally configured cis-stilbene/fluorene hybrid material of the present invention can be fabricated by treating certain chemical reaction method to the key intermediate product of clear crystalline materials represented by the chemical formula 1, such as Hartwig reaction and Rosemund-VonBarann method. Therefore, the exemplary embodiments 1-4 of the spirally configured cis-stilbene/fluorene hybrid materials are represented by following chemical formula II, chemical formula III, chemical formula IV, or chemical formula V:

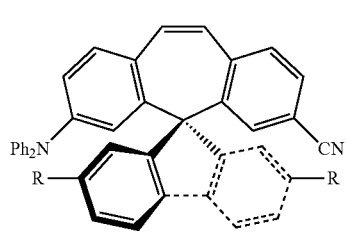

[chemical formula II]

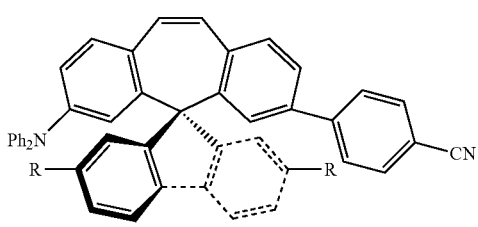

[chemical formula III]

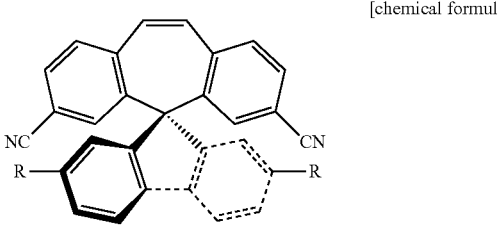

[chemical formula IV]

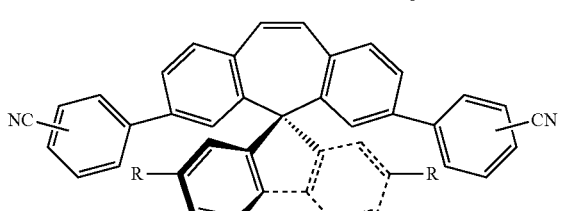

[chemical formula V]

In the chemical II-V, R can be hydrogen group or tert-butyl group. Moreover, the data of glass transition temperature ($T_g$), decomposition temperature ($T_d$), the longest peak wavelength value of absorption spectrum ($\lambda_{max}$), and the longest peak wavelength value of photoluminescence spectrum (PL $\lambda_{max}$) are measured and recorded in the following Table (1). From the Table (1), it is able to know that the spirally configured cis-stilbene/fluorene hybrid materials proposed by the present invention has glass transition temperatures ($T_g$) ranged from 105° C. to 130° C. and decomposition temperatures ($T_d$) ranged from 385° C. to 415° C. That means these spirally configured cis-stilbene/fluorene hybrid materials possess excellent thermal stability, and are not easy to decompose under high voltage and high current density operation conditions.

TABLE (1)

| Group | $T_g$ (° C.) | $T_d$ (° C.) | $\lambda_{max}$ (nm) | PL$\lambda_{max}$ (nm) |
| --- | --- | --- | --- | --- |
| Embodiment 1 (NSCN) | 105 | 390 | 420 | 519 |
| Embodiment 2 (NSΦCN) | 130 | 385 | 410 | 523 |
| Embodiment 3 (CNSCN) | 110 | 415 | 344 | 413 |
| Embodiment 4 (CNΦSΦCN) | 121 | 405 | 365 | 423 |

Moreover, the oxidation potential and the redox potential of the embodiments 1-4 of the spirally configured cis-stilbene/fluorene hybrid materials can be measured by way of cyclic voltammetry (CV); therefore, the highest occupied molecular orbital energy level ($E_{HOMO}$) and lowest unoccupied molecular orbital energy level ($E_{LUMO}$) of the embodiments 1-4 of the spirally configured cis-stilbene/fluorene hybrid materials can also be calculated based on the measured oxidation potential ($E_{1/2}^{ox}$) and the redox potential ($E_{1/2}^{red}$). With reference to following Table (2), $E_{1/2}^{ox}$, $E_{1/2}^{red}$, $E_{HOMO}$, and $E_{LUMO}$ of the spirally configured cis-stilbene/fluorene hybrid materials are recorded. From the Table (2), we are able to know that the spirally configured cis-stilbene/fluorene hybrid materials proposed by the present invention have the $E_{HOMO}$ ranged from 5.4 eV to 6.3 eV and the $E_{LUMO}$ ranged from 2.7 eV to 3.4 eV. Moreover, the spirally configured cis-stilbene/fluorene hybrid materials also have the oxidation potentials ranged from 0.45 V to 1.03 V and the redox potentials ranged from −1.57 V to −2.32 V.

TABLE (2)

| Group | $E_{1/2}^{ox}$ (V) | $E_{1/2}^{red}$ (V) | Eg (eV) | $E_{HOMO}$ (eV) | $E_{LUMO}$ (eV) |
| --- | --- | --- | --- | --- | --- |
| Embodiment 1 (NSCN) | 0.48 | −2.20 | 2.68 | 5.4 | 2.8 |
| Embodiment 2 (NSΦCN) | 0.45 | −1.57 | 2.37 | 5.4 | 2.7 |
| Embodiment 3 (CNSCN) | — | −1.90 | 3.22 | 6.3 | 3.1 |
| Embodiment 4 (CNΦSΦCN) | 1.03 | −2.32 | 3.04 | 6.2 | 3.4 |

In order to prove that the proposed spirally configured cis-stilbene/fluorene hybrid materials can indeed be applied in OLEDs for being as an electron transport layer and/or a hole blocking layer, a plurality of OLED devices for control groups and experiment groups have been designed and manufactured, wherein the constituting layers for the OLED devices are integrated in the following Table (3).

TABLE (3)

| Device Group | substrate | bottom electrode | electron transport layer | hole blocking layer | Light emitting layer | Hole transport layer | top electrode |
|---|---|---|---|---|---|---|---|
| Experiment 1 | Al | LiF | NSCN | BCP | yellow fluorescent | NPB | Al |
| Experiment 2 | Al | LiF | NSΦCN | BCP | yellow fluorescent | NPB | ITO |
| Control 1 | Al | LiF | Alq$_3$ | BCP | yellow fluorescent | NPB | ITO |
| Experiment 3 | Al | LiF | NSCN | BCP | red phosphorescent | TAPC | HIL/ITO |
| Control 2 | Al | LiF | TPBi | BCP | yellow fluorescent | TAPC | HIL/ITO |
| Experiment 4 | Al | LiF | NSCN | BmPyPb | yellow phosphorescent | TAPC | HIL/ITO |
| Control 3 | Al | LiF | Alq$_3$ | BmPyPb | yellow phosphorescent | TAPC | HIL/ITO |
| Experiment 5 | Al | LiF | NSCN | NSCN | green phosphorescent | TAPC | HIL/ITO |
| Experiment 6A | Al | LiF | CNSCN | CNSCN | green phosphorescent | TAPC | HIL/ITO |
| Control 4A | Al | LiF | BmPyPb | BmPyPb | green phosphorescent | TAPC | HIL/ITO |
| Control 4B | Al | LiF | DPyPA | DPyPA | green phosphorescent | TAPC | HIL/ITO |
| Control 4C | Al | LiF | TPBi | TPBi | green phosphorescent | TAPC | HIL/ITO |
| Control 4D | Al | LiF | Alq$_3$ | Alq$_3$ | green phosphorescent | TAPC | HIL/ITO |
| Experiment 7 | Al | LiF | NSCN | NSCN | green phosphorescent | NPB/HT01 | HIL/ITO |
| Control 5 | Al | LiF | BmPyPb | BmPyPb | green phosphorescent | NPB/HT01 | HIL/ITO |
| Control 6 | Al | LiF | ET 01 | ET 01 | green phosphorescent | NPB/HT01 | HIL/ITO |

In the Table (3), BCP is the abbreviation of 2,9-dimethyl-4,7-diphenyl-1,10-phenanthroline, BmPyPb is the abbreviation of 1,3-bis(3,5-dipyrid-3-yl-phenyl)benzene, DPyPA is the abbreviation of 9,10-bis(3-(pyridin-3-yl)phenyl)anthracene, TPBi is the abbreviation of 1,3,5-Tris(1-phenyl-1H-benzimidazol-2-yl)benzene, and Alq$_3$ is the abbreviation of tris(8-hydroxyquinoline) aluminium(iii). In addition, ET 01 is represented by following chemical formula 2″.

[chemical formula 2″]

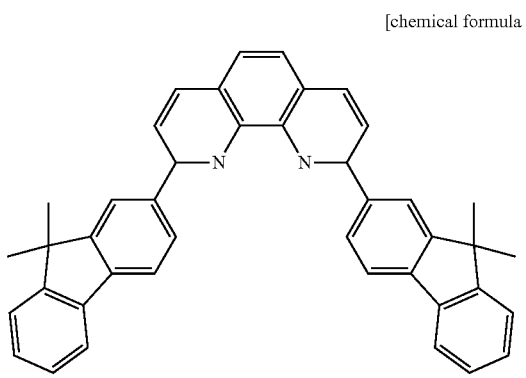

From the Table (3), it is able to know that the materials of Alq$_3$, TPBi, BmPyPb, and ET 01 records in the Table (3) are also used as OLED device's electron transport layers. Continuously, the turn-on voltage ($V_{on}$), the external quantum efficiency ($\eta_{ext}$), the current efficiency ($\eta_c$), the power efficiency ($\eta_p$), and the maximum luminance ($L_{max}$) of the OLED devices have been measured and recorded in the following Table (4).

TABLE (4)

| Device Group | $\lambda_{max}$ (nm) | Von (V) | $\eta_{ext}$ (%) | $\eta_c/\eta_p$ (%) | $L_{max}$ (cd/m$_2$) |
|---|---|---|---|---|---|
| Experiment 1 | 586 | 3.3 | 4.2 | 12.3/6.3 | 32400 |
| Experiment 2 | 586 | 3.6 | 5.0 | 10.6/4.8 | 22830 |
| Control 1 | 581 | 3.4 | 2.7 | 7.1/3.6 | 16660 |
| Experiment 3 | 624 | 3.4 | 20.6 | 18.5/14.7 | 9671 |
| Control 2 | 620 | 3.4 | 16.1 | 15.8/12.2 | 5820 |
| Experiment 4 | 582 | 2.6 | 24.8 | 78.2/79.6 | 78350 |
| Control 3 | 583 | 3.0 | 18.6 | 60.2/53.6 | 49030 |
| Experiment 5 | 520 | 2.9 | 17.0 | 59.1/64.1 | 102600 |
| Experiment 6A | 516 | 3.0 | 12.0 | 36.4/27.6 | 115800 |
| Control 4A | 516 | 2.5 | 6.3 | 22.8/18.0 | 142100 |
| Control 4B | 516 | 3.0 | 10.2 | 37.8/24.0 | 40700 |
| Control 4C | 516 | 3.0 | 6.9 | 24.7/22.0 | 37640 |
| Control 4D | 516 | 2.8 | 3.4 | 11.5/9.7 | 42140 |
| Experiment 7 | 516 | 5.5 | 12.6 | 43.1/24.6 | 22450 |
| Control 5 | 516 | 4.5 | 10.8 | 36.8/25.7 | 42150 |
| Control 6 | 516 | 5.5 | 9.9 | 33.5/19.1 | 25700 |

With reference to the measured data of the yellow fluorescent OLED devices in the Table (4), one can find that the yellow fluorescent OLED devices of Experiment 1 and Experiment 2 show excellent $\eta_{ext}$, $\eta_c$, $\eta_p$, and $L_{max}$ and is much superior to the yellow fluorescent OLED device of Control 1.

Next, please refer to the measured data of the red phosphorescent OLED devices in the Table (4). The measured data obvious reveal that the red phosphorescent OLED devices of Experiment 3 show excellent $\eta_{ext}$, $\eta_p$, and $L_{max}$ and is much superior to the red phosphorescent OLED device of Control 2.

Continuously referring to the measured data of the yellow phosphorescent OLED devices in the Table (4), it can also find that the yellow phosphorescent OLED devices of Experiment 4 show excellent $\eta_{ext}$, $\eta_c$, $\eta_p$, and $L_{max}$ and is much superior to the yellow phosphorescent OLED device of Control 3.

Eventually, please refer to the measured data of the green phosphorescent OLED devices in the Table (4). The measured data reveal that the green phosphorescent OLED devices of Experiment 5 and Experiment 6A show excellent $\eta_{ext}$, $\eta_p$, and $L_{max}$ and are superior to the green phosphorescent OLED device of Control 4A, Control 4B, Control 4C, and Control 4D. Moreover, the green phosphorescent OLED devices of Experiment 7 shows excellent $\eta_{ext}$, $\eta_p$, and $L_{max}$ and is superior to the green phosphorescent OLED device of Control 5 and Control 6.

Furthermore, device life time evaluation test for the green phosphorescent OLEDs have also been completed based on a starting luminance of 10,000 cd/cm². Life time evaluation test results reveal that the decay half lifetime ($LT_{50}$) of the green phosphorescent OLED of Experiment 5 is 19,000 hours. In addition, the decay half lifetime ($LT_{50}$) of the green phosphorescent OLEDs of Control 4A and Control 6 are respectively 1,000 hours and 20,000 hours. Moreover, after replacing the BmPyPb in the green phosphorescent OLEDs of Control 4A by the TmPyPb, the green phosphorescent OLEDs having the TmPyPb material is measured with the $LT_{50}$ of only 210 hours.

Therefore, through above descriptions, the spirally configured cis-stilbene/fluorene hybrid materials for OLEDs proposed by the present invention have been introduced completely and clearly; in summary, the present invention includes the advantages of:

(1) The spirally configured cis-stilbene/fluorene hybrid materials are spirally-configured cis-stilbene/fluorene derivatives having the functions to block holes and constructed by at least one cis-Stilbene based component and at least one fluorene based component, which include glass transition temperatures ranged from 105° C. to 130° C., decomposition temperatures ranged from 385° C. to 415° C., reversible electron transport property, and balanced charges motilities.

(2) Moreover, a variety of experimental data have proved that the yellow fluorescent, the green phosphorescent, the yellow phosphorescent, and the red phosphorescent OLEDs using this spirally configured cis-stilbene/fluorene derivatives as the electron transport layers having hole blocking functions can indeed show excellent EQE, current efficiency, power efficiency, maximum luminance, and device lifetime performances better than the conventional or commercial yellow fluorescent, green phosphorescent, yellow phosphorescent, and red phosphorescent OLEDs.

The above description is made on embodiments of the present invention. However, the embodiments are not intended to limit scope of the present invention, and all equivalent implementations or alterations within the spirit of the present invention still fall within the scope of the present invention.

What is claimed is:

1. A spirally configured cis-stilbene/fluorene hybrid material for OLED device, wherein the spirally configured cis-stilbene/fluorene hybrid material is spirally-configured cis-stilbene/fluorene compound having the function to block holes and constructed by at least one cis-Stilbene based component and at least one fluorene based component, wherein the spirally configured cis-stilbene/fluorene hybrid material is represented by following chemical formula V:

[chemical formula V]

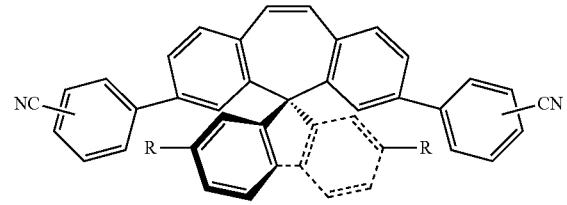

wherein, R is hydrogen group or tert-butyl group.

2. The spirally configured cis-stilbene/fluorene hybrid material of claim 1, having glass transition temperatures ($T_g$) ranged from 105° C. to 130° C. and decomposition temperatures ($T_d$) ranged from 385° C. to 415° C.

3. The spirally configured cis-stilbene/fluorene hybrid material of claim 1, having highest occupied molecular orbital energy level ($E_{HOMO}$) ranged from 5.4 eV to 6.3 eV and lowest unoccupied molecular orbital energy level ($E_{LUMO}$) ranged from 2.7 eV to 3.4 eV.

4. The spirally configured cis-stilbene/fluorene hybrid material of claim 1, capable of being applied in the OLED device for being as an electron transport layer and/or a hole blocking layer.

5. The spirally configured cis-stilbene/fluorene hybrid material of claim 1, capable of being applied in a solar cell for being as a carrier transport layer.

6. The spirally configured cis-stilbene/fluorene hybrid material of claim 1, having oxidation potentials ranged from 0.45V to 1.03V and redox potentials ranged from −1.57V to −2.32V.

7. The spirally configured cis-stilbene/fluorene hybrid material of claim 1, wherein the spirally configured cis-stilbene/fluorene hybrid material is represented by following chemical formula V-1:

[chemical formula V-1]

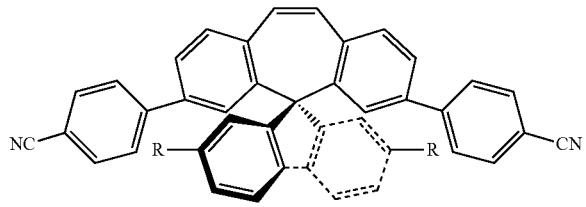

wherein R is hydrogen group or tert-butyl group.

8. The spirally configured cis-stilbene/fluorene hybrid material of claim 1, wherein the spirally configured cis-stilbene/fluorene hybrid material is represented by following chemical formula V-2:

[chemical formula V-2]
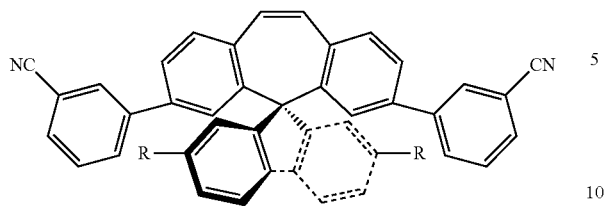
wherein R is hydrogen group or tert-butyl group.
9. The spirally configured cis-stilbene/fluorene hybrid material of claim 1, wherein the spirally configured cis-stilbene/fluorene hybrid material is represented by following chemical formula V-3:
[chemical formula V-3]
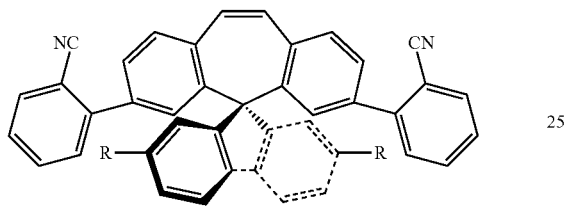
wherein R is hydrogen group or tert-butyl group.
* * * * *